US011053474B2

(12) United States Patent
Goelling et al.

(10) Patent No.: US 11,053,474 B2
(45) Date of Patent: Jul. 6, 2021

(54) LACTOBACILLUS STRAINS AND THE USES THEREOF

(71) Applicant: NOVOZYMES A/S, Bagsvaerd (DK)

(72) Inventors: Detlef Goelling, Hattstedt (DE); Andreas Heilmann, Berlin (DE); Christine Lang, Berlin (DE)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/774,713

(22) PCT Filed: Mar. 12, 2014

(86) PCT No.: PCT/EP2014/054879
§ 371 (c)(1),
(2) Date: Sep. 11, 2015

(87) PCT Pub. No.: WO2014/140123
PCT Pub. Date: Sep. 18, 2014

(65) Prior Publication Data
US 2016/0024459 A1    Jan. 28, 2016

Related U.S. Application Data

(60) Provisional application No. 61/779,246, filed on Mar. 13, 2013.

(30) Foreign Application Priority Data

Mar. 13, 2013  (EP) .................................... 13159061

(51) Int. Cl.

| | | |
|---|---|---|
| *A01N 63/00* | (2020.01) | |
| *A23K 10/18* | (2016.01) | |
| *A23L 3/3571* | (2006.01) | |
| *A61K 8/99* | (2017.01) | |
| *A61K 35/74* | (2015.01) | |
| *A61K 35/747* | (2015.01) | |
| *A61Q 19/00* | (2006.01) | |
| *C12N 1/20* | (2006.01) | |
| *C12R 1/24* | (2006.01) | |
| *C12R 1/25* | (2006.01) | |
| *C12R 1/225* | (2006.01) | |
| *A23C 9/123* | (2006.01) | |
| *A23L 29/00* | (2016.01) | |

(52) U.S. Cl.
CPC ............. *C12N 1/20* (2013.01); *A01N 63/00* (2013.01); *A23C 9/1234* (2013.01); *A23K 10/18* (2016.05); *A23L 3/3571* (2013.01); *A23L 29/065* (2016.08); *A61K 8/99* (2013.01); *A61K 35/74* (2013.01); *A61Q 19/00* (2013.01); *C12R 1/24* (2013.01); *A23V 2002/00* (2013.01); *A23Y 2220/00* (2013.01); *A23Y 2220/13* (2013.01); *A23Y 2220/67* (2013.01); *A61K 2800/10* (2013.01); *A61K 2800/85* (2013.01); *C12R 1/225* (2013.01); *C12R 1/25* (2013.01)

(58) Field of Classification Search
None
See application file for complete search history.

(56) References Cited

U.S. PATENT DOCUMENTS

| | | | |
|---|---|---|---|
| 5,053,233 A | 10/1991 | Setala et al. | |
| 6,612,809 B2 | 9/2003 | Czachor et al. | |
| 6,742,852 B2 | 6/2004 | Tsuru et al. | |
| 6,959,621 B1 | 11/2005 | Walther | |
| 2005/0125036 A1 | 6/2005 | Roby | |
| 2005/0196480 A1 | 9/2005 | Sullivan et al. | |
| 2009/0130073 A1* | 5/2009 | Reindl .................. | A61K 35/74 424/93.45 |
| 2011/0038837 A1 | 2/2011 | Nishida et al. | |
| 2011/0045134 A1 | 2/2011 | Perrier et al. | |

FOREIGN PATENT DOCUMENTS

| | | | | |
|---|---|---|---|---|
| CN | 102093965 | | 11/2010 | |
| CN | 102747009 | | 4/2012 | |
| EP | 1133046 | A2 | 12/2001 | |
| EP | 1251064 | A1 | 10/2002 | |
| EP | 1316677 | A1 | 6/2003 | |
| EP | 1506789 | A1 | 2/2005 | |
| EP | 1218230 | B1 | 3/2005 | |
| EP | 2 543 246 | A1 | 1/2013 | |
| EP | 2543246 | A1 | 1/2013 | |
| EP | 2 592 158 | A1 | 5/2013 | |
| EP | 2592158 | A1 * | 5/2013 | ............... A23L 3/00 |
| IE | 2592158 | A1 * | 5/2013 | ............. A01N 63/02 |
| JP | H107-115948 | | 10/1993 | |
| JP | H108-289770 | | 4/1995 | |
| JP | 2009-261249 | | 11/2009 | |
| WO | 8901970 | A2 | 3/1989 | |
| WO | 1994019950 | A1 | 9/1994 | |

OTHER PUBLICATIONS

Muynck et al., Microbiological Research, vol. 159, pp. 339-346 (2004).*
Muyncketal., Microbiological Research, vol. 159, pp. 339-346 (2004)(of record).*
Muyncketal., Microbiological Research, vol. 159, pp. 339-346 (2004)(of record) (Year: 2004).*
Annuk, H. et al., Characterisation and differentiation of lactobacilli by lectin typing, J. Med. Microbiol., vol. 50 (2001), pp. 1069-1074.
Ausubel, Current Protocols in Molecular Biology, 1989, Green Publishing Associates and Wiley Interscience, NY.
Corsetti, A. et al., Antimould Activity of Sourdough Lactic Acid Bacteria: Identification of a Mixture of Organic Acids Produced by Lactobacillus sanfrancisco CB1, Appl. Microbiol. Biotechnol. (1998) 50, pp. 253-256.

(Continued)

*Primary Examiner* — Soren Harward
*Assistant Examiner* — Paul D. Pyla
(74) *Attorney, Agent, or Firm* — Eric Fechter

(57) ABSTRACT

The invention concerns novel *Lactobacillus* strains and the uses thereof, in particular for preserving foods, animal feedstuff, pharmaceutical compositions and/or cosmetic compositions.

8 Claims, 5 Drawing Sheets

Specification includes a Sequence Listing.

(56) References Cited

OTHER PUBLICATIONS

Diep, D.B. et al., The Synthesis of the Bacteriocin Sakacin A is a Temperature-Sensitive Process Regulated by a Pheromone Peptide Through a Three-Component Regulatory System, Microbiology (2000), 146, pp. 2155-2160.

El-Nezami, H. et al., Physicochemical Alterations Enhance the Ability of Dairy Strains of Lactic Acid Bacteria to Remove Aflatoxin from Contaminated Media, Journal of Food Protection, vol. 61, No. 4, 1998, pp. 466-468.

Falguni, P. et al., Productions of Proteinaceous Antifungal Substances Form Lactobacillus brevis NDCD 02, International Journal of Dairy Technology, 2010, vol. 63, pp. 70-76.

Gatti, M. et al., Cell-wall Protein Profiles of Dairy Thermophilic Lactobacilli, Letters in Applied Microbiology, 1997, vol. 25, pp. 345-348.

Gevers, D. et al., Applicability of rep-PCR fingerprinting for identification of Lactobacillus species, FEMS Microbiology Letters, vol. 205, 2001, pp. 31-36.

Giraffa, G. et al., Molecular typing of Lactobacillus delbrueckii of dairy origin by PCR-RFLP of protein-coding genes, International Journal of Food Microbiology, vol. 82, 2003, pp. 163-172.

Heyrman, J. et al., The use of fatty acid methyl ester analysis (FAME) for the identification of heterotrophic bacteria present on three mural paintings showing severe damage by microorganisms, FEMS Microbiology Letters, vol. 181, 1999, pp. 55-62.

Kersters, K., Numerical Methods in the Classification and Identification of Bacteria by Electrophoresis, Computer-Assisted Bacterial Systematics, 1985, pp. 337-368, M. Goodfellow, A.G. O'Donnell Ed., John Wiley and Sons Ltd.

Kleerebezem, M. et al., A two-component signal-transduction cascade in Carnobacterium piscicola LV17B: two signaling peptides and one sensor-transmitter, Peptides, vol. 22, 2001, pp. 1597-1601.

Lavermicocca, P. et al., Purification and Characterization of Novel Antifungal Compounds from the Sourdough Lactobacillus plantarum Strain 21B, Applied and Environmental Microbiology, vol. 66, No. 9, 2000, pp. 4084-4090.

Ludwig, W. et al., Complete 23S ribosomal RNA sequences of Gram-positive bacteria with a low DNA G+C content, System. Appl. Microbiol., vol. 15, 1992, pp. 487-501.

Magnusson, J. et al., Lactobacillus coryniformis subsp. coryniformis Strain Si3 Produces a Broad-Spectrum Proteinaceous Antifungal Compound, Applied and Environmental Microbiology, vol. 67, No. 1, 2001, pp. 1-5.

Maldonado, A. et al., Induction of Plantaricin Production in Lactobacillus plantarum NC8 after Coculture with Specific Gram-Positive Bacteria is Mediated by an Autoinduction Mechanism, Journal of Bacteriology, vol. 186, No. 5, 2004, pp. 1556-1564.

Matsuguchi, T. et al., Lipoteichoic Acids from Lactobacillus Strains Elicit Strong Tumor Necrosis Factor Alpha-Inducing Activities in Macrophages through Toll-Like Receptor 2, Clinical and Diagnostic Laboratory Immunology, vol. 10, No. 2, 2003, pp. 259-266.

Nilsen, T. et al., An Exported Inducer Peptide Regulates Bacteriocin Production in Enterococcus faecium CTC492, Journal of Bacteriology, vol. 180, No. 7, 1998, pp. 1848-1854.

Nigatu, A. et al., Randomly amplified polymorphic DNA (RAPD) profiles for the distinction of Lactobacillus species, Antonie van Leeuwenhoek, vol. 79, 2001, pp. 1-6.

Niku-Paavola, M.L. et al., New Types of Antimicrobial Compounds Produced by Lactobacillus plantarum, Journal of Applied Mirobiology, vol. 86, 1999, pp. 29-35.

Rollan, G. et al., The peptide hydrolase system of Lactobacillus reuteri, International Journal of Food Microbiology, vol. 70, 2001, pp. 303-307.

Schleifer, K.H. et al., Phylogeny of the Genus Lactobacillus and Related Genera, System. Appl. Microhiol., vol. 18, 1995, pp. 461-467.

Sjoegren, J. et al., Antifungal 3-Hydroxy Fatty Acids from Lactobacillus plantarum MiLAB 14, Applied and Environmental Microbiology, vol. 69, No. 12, 2003, pp. 7554-7557.

Varmanen, P. et al., X-Prolyl Dipeptidyl Aminopeptidase Gene (pepX) is Part of the glnRA Operon in Lactobacillus rhamnosus, Journal of Bacteriology, vol. 182, No. 1, 2000, pp. 146-154.

Stentz, R. et al., Development of Genetic Tools for Lactobacillus sakei: Disruption of the b-Galactosidase Gene and Use of lacZ as a Reporter Gene to Study Regulation of the Putative Copper ATPase, AtkB, Applied and Environmental Microbiology, vol. 66, No. 10, 2000, pp. 4272-4278.

Raspor, P. et al., Biocontrol of Grey Mould Disease on Grape Caused by Botrytis cinerea with Autochthonous Wine Yeasts, Food Technol. Biotechnol., vol. 48, No. 3, 2010, pp. 336-343.

Patra Falguni et al: "Production of proteinaceous antifungal substances from Lactobacillus brevis NCDC 02", in: International Journal of Dairy Technology, vol. 63, No. 1, Feb. 1, 2010, pp. 70-76.

C. Plumed-Ferrer et al: "Comparative Study of Sugar Fermentation and Protein Expression Patterns of Two Lactobacillus plantarum Strains Grown in Three Different Media", in: Applied and Environmental Microbiology, vol. 74, No. 17, Jun. 20, 2008, pp. 5349-5358.

Ronka E et al: "Probiotic and Milk Technological Properties of Lactobacillus brevis" in: International Journal of Food Microbiology, Elsevier BV, NL, vol. 83, No. 1, Jan. 1, 2003, pp. 63-74.

Klewicka, 2007, Acta Alimentaria 36(4), 495-499.

Zhang et al, 2008, China Dairy Industry 33(6), 31-37.

* cited by examiner

Fig. 5

| Incubation-time [h] | without Lactobacillus | with negative Lactobacillus strain | with Lactobacillus DSM 22721 |
|---|---|---|---|
| 14 | 91,82 | 88,10 | 2,68 |
| 18 | 94,39 | 94,64 | 0,00 |
| 20 | 97,41 | 90,76 | 3,54 |
| 22 | 93,33 | 96,69 | 2,75 |
| 24 | 95,16 | 96,19 | 0,96 |

SEQUENCE LISTING

<160> NUMBER OF SEQ ID NOS: 1

<210> SEQ ID NO 1
<211> LENGTH: 951
<212> TYPE: DNA
<213> ORGANISM: Lactobacillus brevis

<400> SEQUENCE: 1 gcgactttc ggattattgg gcgtaaagcg agcgcaggcg gtttttagg tctgatgtga      60 aagccttcgg cttaaccgga gaagggcatc ggaaaccggg agacttgagt gcagaagagg     120

```
acagtggaac tccatgtgta gcggtgaaat gcgtagatat atggaagaac accagtggcg        180
aaggcggctg tctggtctgt aactgacgct gaggctcgaa agcatgggta gcgaacagga        240
ttagataccc tggtagtcca tgccgtaaac gatgagtgct aagtgttgga gggtttccgc        300
ccttcagtgc tgcagctaac gcattaagca ctccgcctgg ggagtacgac cgcaaggttg        360
aaactcaaag gaattgacgg gggcccgcac aagcggtgga gcatgtggtt taattcgatg        420
ctacgcgaag aaccttacca ggtcttgaca tcttctgcta acctaagaga ttaggcgttc        480
ccttcgggga cggaatgaca ggtggtgcat ggttgtcgtc agctcgtgtc gtgagatgtt        540
gggttaagtc ccgcaacgag cgcaaccctt attgtcagtt gccagcattt agttgggcac        600
tctggcgaga ctgccggtga caaaccggag gaaggtgggg atgacgtcaa atcatcatgc        660
cccttatgac ctgggctaca cacgtgctac aatggacggt acaacgagtc gcgaaaccgc        720
gaggtcaagc taatctctta aagccgttct cagttcggat tgcaggctgc aactcgcctg        780
catgaagttg gaatcgctag taatcgtgga tcagcatgcc acggtgaata cgttcccggg        840
cccttgtaca caccgcccgt cacaccatga gagtttgtaa cacccaaagc ccgtgaggta        900
accttcggga accagccgtc taagtgggac agatgattag gtgaagtcga c                951
```

LACTOBACILLUS STRAINS AND THE USES THEREOF

CROSS-REFERENCE TO RELATED APPLICATIONS

This is the U.S. national stage of International application PCT/EP2014/054879, filed Mar. 12, 2014 designating the United States and claiming the benefit of U.S. provisional application 61/779,246, filed Mar. 13, 2013 and claiming priority to European application 13159061.4, filed Mar. 13, 2013.

INCORPORATION OF SEQUENCE LISTING

The sequence listing was created as a text file as part of International application PCT/EP2014/054879, on Mar. 20, 2014 and filed therein is hereby incorporated by reference. An extra copy of this text file named "eolf-seql.txt", which is 2 kilobytes (measured in MS-WINDOWS), dated Sep. 11, 2015 was downloaded from WIPO and is submitted herewith via the USPTO EFS system.

FIELD OF THE INVENTION

The invention concerns novel *Lactobacillus* strains and the uses thereof, in particular for preserving foods, animal feedstuff, pharmaceutical compositions and/or cosmetic compositions.

PRIOR ART AND BACKGROUND OF THE INVENTION

Foods and animal feedstuff are, due to their nutritious composition, good substrates for microorganisms. Similar considerations apply for pharmaceutical and cosmetic compositions because of the galenic substances or carrier and auxiliary substances often contained therein. Many of these microorganisms, in particular fungi, are one of the most frequent reasons for the spoilage of foods and animal feedstuff, but also of pharmaceutical or cosmetic compositions. Particularly critical are especially the toxic and carcinogenic mycotoxins formed by the microorganisms, which are dangerous to the health of humans. Besides this effect, the spoilage of foods has an enormous economic impact every year. It is assumed that approx. 5-10% of the foods are destroyed due to microbial spoilage every year.

In order to avoid spoilage of for instance foods and animal feedstuff, they are made more durable by processing or addition of chemical or biological preservation agents. The demand for biological preservation agents in particular is increasing, since many consumers seek to avoid chemical preservation agents.

To these biological preservation agents belong e.g. the lactic acid bacteria. These bacteria are normally harmless to man and have historically been used for centuries in the preservation of food. Their safety and harmlessness is expressed by their so-called GRAS status (generally recognized as safe) from the American FDA (Food and Drug Administration). Additionally in many foods, lactic acid bacteria occur naturally already.

The mechanism of biopreservation can either be caused by competitive growth or the biosynthesis of antagonistic and antimicrobial metabolites. Primarily, the preservative effect of lactic acid bacteria is due to the generation of organic acids such as lactic acid. Thereby, the pH value is reduced, which inhibits the growth of many microorganisms.

Besides lactic acid, there is a series of other metabolites such as acetic acid, hydrogen peroxide, diacetyl, reuterin and so-called bacteriocins that are important for the preservation of foods and animal feedstuff.

Some of these metabolites, such as lactic acid and reuterin, inhibit the growth of bacteria and fungi, other substances, such as bacteriocins, inhibit exclusively the growth of bacteria, and again other substances only act against fungi. In studies concerning the antifungal activity of lactic acid bacteria, numerous inhibitory substances could be identified: caproic, propionic, butyric, acetic, formic and valerianic acid (Corsetti, A. G., Antimould activity of sourdough lactic acid bacteria: identification of a mixture of organic acids produced by *Lactobacillus sanfrancisco* CB1, Applied Microbiology and Biotechnology (50), pp. 253-256, (1998)), methylhydantoin and mevalonolactone (Niku-Paavola, M. L., New types of antimicrobial compounds produced by *Lactobacillus plantarum*, Journal of Applied Microbiology (86), pp. 29-35, (1999), various hydroxy fatty acids (Sjögren, J. M., Antifungal 3-hydroxy fatty acids from *Lactobacillus plantarum* MiLAB 14, Applied and Environmental Microbiology (69), pp. 7554-7557, (2003)), 3-phenyl lactic acid (Lavermicocca, P. V., Purification and characterization of novel antifungal compounds from the sourdough *Lactobacillus plantarum* strain 21B, Applied and Environmental Microbiology (66), pp. 4084-90, (2000), and diketopiperazines (Niku-Paavola, see above). Some proteinogenic components with antifungal activity could not be identified, however (Magnusson, J., *Lactobacillus coryniformis* subsp. *coryniformis* strain Si3 produces a broad-spectrum proteinaceous antifungal compound, Applied and Environmental Microbiology (67), pp. 1-5, (2001)).

Whilst many of the metabolites are formed accompanying the cell growth of the lactic acid bacteria, it is known that others are only generated after an induction. This mechanism is generally called autoinduction or "quorum sensing". This effect is known for some bacteriocins already such as *Carnobacterium piscicola* (Kleerebezem, M. K., A two-component signal transduction cascade in *Carnobacterium piscicola* LV17B: two signaling peptides and one sensor-transmitter, Peptides (22), pp. 1597-1601, (2003)), *Lactobacillus sakei* (Diep, D. B., The synthesis of the bacteriocin sakacin A is a temperature-sensitive process regulated by a pheromone peptide through a three-component regulatory system, Microbiology (146), pp. 2155-2160, (2000)), *Lactobacillus plantarum* (Maldonado, A. J.-D., Induction of Plantaricin Production in *Lactobacillus plantarum* NC8 after Coculture with Specific Gram-Positive Bacteria Is Mediated by an Autoinduction Mechanism, J. Bacteriol., 5 (186), pp. 1556-1564 (2003)) and *Enterococcus faecium* (Nilsen, T. I., An exported inducer peptide regulates bacteriocin production in *Enterococcus faecium* CTC 492, J. Bacteriol. (180), pp. 1848-1854, (1998)).

Bacteria of the species *Burkholderia* and *Pseudomonas* do not have, however, GRAS status and are therefore not suitable for use in foods or animal feedstuff.

Patra Falguni et al ("Productions of proteinaceous antifungal substances form *Lactobacillus brevis* NDCD 02", International Journal of Dairy Technology vol. 63, No. 1, 1 Feb. 2010, pages 70-76), discloses a *Lactobacillus brevis* strain with a broad antifungal spectrum, which may be used as an effective bio preservative and non starter LAB in food. A major limitation of this strain is that it needs nutrient rich medium to produce antifungal substances. For example the production of antifungal substances was negligible in skim milk. Therefore this *Lactobacillus brevis* strain is not suitable for the use as a food additive in dairy products.

EP 2543246 discloses the antifungal effect of viable bacteria of *Lactobacillus plantarum* strain against *Penicillium* and *Aspergillus* in a cheese coating. Therefore the antifungal effect occurred under aerobic conditions. An antifungal effect under anaerobic conditions was not shown. But for the use as a food additive in dairy products it is important that an antifungal effect is present under aerobic and anaerobic conditions.

Given this background, it would be desirable to provide GRAS-recognized microorganisms, which form antifungal metabolites, inhibit the growth of fungi and are thus suitable as preservation agents without the limitations and disadvantages of the state of the art.

TECHNICAL OBJECTIVE OF THE INVENTION

It is therefore the technical objective of the invention to provide microorganisms that inhibit the growth of fungi and are suitable to be used in foods, animal feedstuff, pharmaceutical and/or cosmetic compositions.

BRIEF DESCRIPTION OF THE FIGURES

FIG. 5 shows the germination rate in [%] of *P. commune* spores after coincubation with and without *Lactobacillus* cells.

BASICS OF THE INVENTION AND PREFERRED EMBODIMENTS

Figure 1:
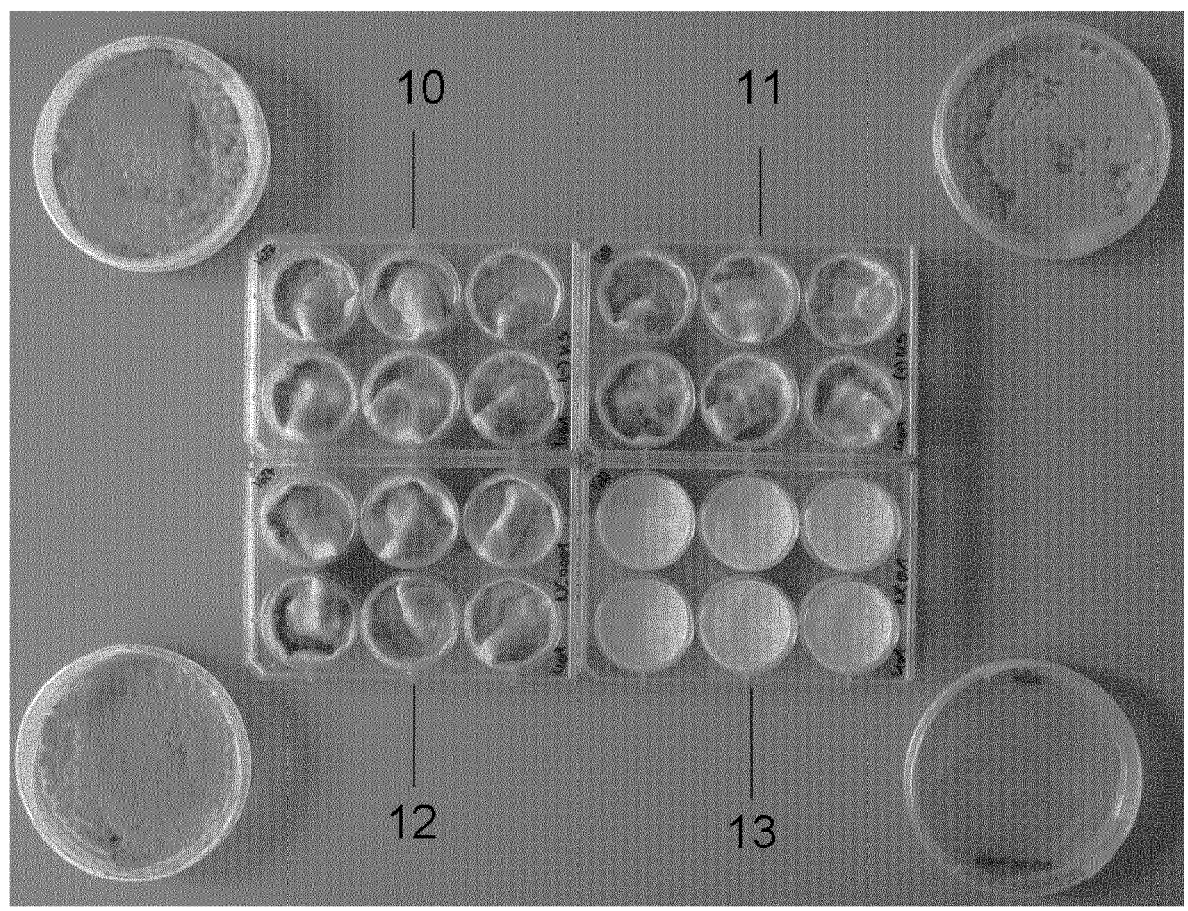
FIG. 1 shows the results of example 2.

This problem is solved by the features of the independent claims. Preferred embodiments of the present invention are provided by the dependent claims.

For achieving this technical objective, the invention teaches a microorganism belonging to the group of lactic acid bacteria or a fragment thereof for use as a food additive, wherein the lactic acid bacterium is heterolactic and wherein the lactic acid bacterium inhibits the growth of at least one fungal organism.

Lactic acid bacteria are from a taxonomical point of view divided up into the subdivisions of *Streptococcus, Leuconostoc, Pediococcus, Lactobacillus* and *Lactococcus*. It is preferred that the microorganism of the present invention is a *Lactobacillus* species. Members of the lactic acid bacteria group normally lack porphyrins and cytochromes, do not carry out electron-transport phosphorylation and hence obtain energy only by substrate-level phosphorylation. I.e. in lactic acid bacteria ATP is synthesized through fermentation of carbohydrates. All of the lactic acid bacteria grow anaerobically, however, unlike many anaerobes, most lactic acid bacteria are not sensitive to oxygen and can thus grow in its presence as well as in its absence. Accordingly, the bacteria of the present invention are preferably aerotolerant anaerobic lactic acid bacteria belonging to the genus of *Lactobacillus*.

The ability to grow under anaerobic conditions is a major advantage compared to the strains known in the state of the art. Therefore it is now possible to use the lactic acid bacteria of the invention as a food additive not only in the coating of dairy products but also in the products themselves like milk, yoghurt or cottage cheese.

The lactic acid bacteria of the invention do not need any special nutritious medium to exhibit its antifungal activity. Experiments showed that the lactic acid bacteria of the invention are also able to inhibit the growth of at least one fungal organism in skim milk. Therefore the lactic acid bacteria of the invention can be used in different kinds of dairy products without adding any extra nutrients which would be a disadvantage for the use as a food additive. Due to this fact the microorganism of the invention is superior compared to the microorganism known in the prior art, especially Patra Falguni et al.

The microorganism belonging to the group of lactic acid bacteria of the present invention is preferably rod-shaped, varying from long and slender to short bent rods, is moreover preferably immotile and/or asporogenous. It is preferred that the lactic acid bacteria of the invention are separated or in pairs. They preferably produce lactic acid as a major or sole product of fermentative metabolism. It is preferred that the lactic acid bacteria of the invention produce lactic acid, preferably the DL-isomer of lactic acid in an amount of at least 50% from glucose via the pentose-phosphate pathway. The lactic acid bacteria of the invention can also produce carbon dioxide and ethanol. It is preferred that the lactic acid bacteria show variable growth at a temperature of 15° C. or 45° C. It is further preferred that they have glycerol teichoic acid in their cell wall.

Based on the above-described characteristics, the lactic acid bacteria of the present invention can be classified to belong to the genus of *Lactobacillus*. By using classical systematics, for example, by reference to the pertinent descriptions in 'Bergey's Manual of Systematic Bacteriology" (Williams & Wilkins Co., 1984), a lactic acid bacterium of the present invention can be determined to belong to the genus of *Lactobacillus*. Alternatively, the lactic acid bacteria of the present invention can be classified to belong to the genus of *Lactobacillus* by methods known in the art, for example, by their metabolic fingerprint, i.e. a comparable overview of the capability of the microorganism(s) of the present invention to metabolize sugars or by other methods described, for example, in Schleifer et al., System. Appl. Microb., 18 (1995), 461-467 or Ludwig et al., System. Appl. Microb., 15 (1992), 487-501. The microorganisms of the present invention are capable of metabolizing sugar sources which are typical and known in the art for microorganisms belonging to the genus of *Lactobacillus*. In a preferred embodiment, however, the lactic acid bacterium of the present invention has a metabolic fingerprint selected from the group consisting of:

(i) it metabolizes D-lactose, but not L-sorbose and/or D-saccharose and/or D-inuline, (ii) it metabolizes inuline, (iii) it metabolizes L-sorbose, but not D-lactose and/or D-saccharose and/or inuline, and (iv) it metabolizes L-sorbose, D-lactose and inuline.

Preferably, the lactic acid bacterium of the present invention has a metabolic fingerprint selected from the group consisting of:

(i) it metabolizes D-lactose, but not L-sorbose, D-saccharose and inuline, (ii) it metabolizes L-sorbose, D-lactose and inuline, but not D-saccharose, (iii) it metabolizes L-sorbose, but not D-lactose, D-saccharose and inuline, and (iv) it metabolizes L-sorbose, D-lactose, D-saccharose, but not inuline.

Of course, the lactic acid bacterium of the present invention is not limited to the metabolization of the sugars mentioned in the aforementioned metabolic fingerprint pattern, but may be capable of metabolizing further sugars which are commonly metabolized by *Lactobacillus* species.

The affiliation of the microorganisms of the present invention to the genus of *Lactobacillus* can also be characterized by using other methods known in the art, for example, using SDS-PAGE gel electrophoresis of total protein of the species to be determined and comparing them to known and already characterized strains of the genus *Lactobacillus*. The techniques for preparing a total protein profile as described above, as well as the numerical analysis of such profiles, are well known to a person skilled in the art. However, the results are only reliable insofar as each stage of the process is sufficiently standardized. Faced with the requirement of accuracy when determining the attachment of a microorganism to the genus of *Lactobacillus*, standardized procedures are regularly made available to the public by their authors such as that of Pot et al., as presented during a "workshop" organized by the European Union, at the University of Ghent, in Belgium, on Sep. 12 to 16, 1994 (Fingerprinting techniques for classification and identification of bacteria, SDS-PAGE of whole cell protein). The software used in the technique for analyzing the SDS-PAGE electrophoresis gel is of crucial importance since the degree of correlation between the species depends on the parameters and algorithms used by this software. Without going into the theoretical details, quantitative comparison of bands measured by a densitometer and normalized by a computer is preferably made with the Pearson correlation coefficient. The similarity matrix thus obtained may be organized with the aid of the UPGMA (unweighted pair group method using average linkage) algorithm that not only makes it possible to group together the most similar profiles, but also to construct dendograms (see Kersters, Numerical methods in the classification and identification of bacteria by electrophoresis, in Computer-assisted Bacterial Systematics, 337-368, M. Goodfellow, A. G. O'Donnell Ed., John Wiley and Sons Ltd, 1985).

Alternatively, the affiliation of said microorganisms of the present invention to the genus of *Lactobacillus* can be characterized with regard to ribosomal RNA in a so called Riboprinter® More preferably, the affiliation of the newly identified species of the invention to the genus *Lactobacillus* is demonstrated by comparing the nucleotide sequence of the 16S ribosomal RNA of the bacteria of the invention, or of their genomic DNA which codes for the 16S ribosomal RNA, with those of other genera and species of lactic acid bacteria known to date. Another preferred alternative for determining the attachment of the newly identified species of the invention to the genus *Lactobacillus* is the use of species-specific PCR primers that target the 16S-23S rRNA spacer region. Another preferred alternative is RAPD-PCR (Nigatu et al. in Antonie van Leenwenhoek (79), 1-6, 2001) by virtue of that a strain specific DNA pattern is generated which allows to determine the affiliation of an identified microorganisms in accordance with the present invention to the genus of *Lactobacillus*. Further techniques useful for determining the affiliation of the microorganism of the present invention to the genus of *Lactobacillus* are restriction fragment length polymorphism (RFLP) (Giraffa et al., Int. J. Food Microbiol. 82 (2003), 163-172), fingerprinting of the repetitive elements (Gevers et al., FEMS Microbiol. Lett. 205 (2001) 31-36) or analysis of the fatty acid methyl ester (FAME) pattern of bacterial cells (Heyrman et al., FEMS Microbial. Lett. 181 (1991), 55-62). Alternatively, lactobacilli can be determined by lectin typing (Annuk et al., J. Med. Microbiol. 50 (2001), 1069-1074) or by analysis of their cell wall proteins (Gatti et al., Lett. Appl. Microbiol. 25 (1997), 345-348).

In a particularly preferred embodiment the present invention relates to an isolated lactic acid bacterium or a fragment thereof prepared by process comprising:
a) providing a substrate,
b) providing a preparation comprising lactic acid bacteria under investigation,
c) adding the preparation comprising the lactic acid bacteria to the substrate, optionally followed by a fermentation step,
d) adding of a predetermined number of fungal spores to the product of step c),
e) incubation of the test sample obtained in step d) for a predetermined duration at a predetermined temperature,
f) detection, optionally followed by evaluation of fungal growth
g) isolation of at least one lactic acid bacterium.

If no fungal growth is detectable, the lactic acid bacterium is a lactic acid bacterium according to the invention. Therefore it is preferred that step g) is performed when no or fungal growth is detectable.

Furthermore, if reduced fungal growth is detected, compared with a control test sample, wherein step c) has been omitted, then the lactic acid bacterium is a species according to the invention as well. Therein the phrase "reduced" means a reduction of fungal growth by at least 20%, better at least 50%, preferably at least 90%.

It is also preferred that the Lactic acid bacterium of the invention is characterized in that it can be assayed according to the following steps:
A) a substrate is established,
B) a preparation comprising lactic acid bacteria under investigation is established,
C) the preparation comprising the lactic acid bacteria is added to the substrate, optionally followed by a fermentation step,
D) the product of step C) is sampled into sample holders, herein test samples are formed,
E) a predetermined number of fungal spores is added to at least one test sample,
F) incubation of the test sample obtained in step E) is performed for a predetermined duration at a predetermined temperature,
G) detection, optionally followed by evaluation of fungal growth.

It is preferred that fungal growth is detected by performing a camera shot or visual inspection of the test sample after step F) and evaluation of fungal growth.

If no fungal growth is detectable, the lactic acid bacterium is a lactic acid bacterium according to the invention. Furthermore, if reduced fungal growth is detected, compared with a control test sample, wherein step C) has been omitted, then the lactic acid bacterium is a species according to the invention as well. Therein the phrase "reduced" means a reduction of fungal growth by at least 20%, better at least 50%, preferably at least 90%. The quantification can be carried out by performing the camera shot at a defined contrast setting and automated count out of pixels related with fungal coverage, wherein the count of pixels related with fungal coverage is related to the total pixel number of the camera shot of the test sample. The camera shot will preferably be in black/white. In some instances it will be helpful to stain the substrate with a dark pigment or colour (which preferably is microbiologically inert) in order to enhance the contrast of fungi over the substrate, for example if the substrate is a yogurt substrate of white colour and the fungi exhibit white colour as well. In particular, the test assay may be performed as outlined in Example 1.2, last paragraph. As a camera the FluorChem® FC2 Imaging System (Alpha Innotech/Cell Biosciences), Santa Clara, USA) system is useful with the following settings: Exposure time: 100-150 ms, aperture: 8, contrast settings: black level: 55000, white level: 60000, gamma: 3.0, light settings: trans-light "on", reflected-light "on", chemi display "on", speed/resolution: normal/ultra. Images were analyzed with the AlphaEaseFC software.

As an alternative or additional control test sample, a test sample may be used, wherein potassium sorbate in a predetermined amount usual in the art of food preservation (e.g. 0.2 mg per gram) is employed in step c) instead of the step c) described above. This control test sample then may serve as a benchmark, i.e. the lactic acid bacteria of the invention effects an inhibition of fungal growth at least to the same amount, as this control test sample.

Cells are viable, if they meet the test for viability of the DSMZ Deutsche Sammlung von Mikroorganismen and Zellkulturen GmbH, Braunschweig, Germany, if applicable in cocultivation with the respective substrate, to which the cells are to be added or on which they are to be applied.

It is preferred that the lactic acid bacterium is a live lactic acid bacterium. It was surprising that the living microorganism according to the invention exhibit a strong antifungal capacity without adversely effect the food product.

It is especially preferred that the lactic acid bacterium is *Lactobacillus brevis, Lactobacillus hilgardii, Lactobacillus plantarum, Lactobacillus fructivorans* or *Lactobacillus parafarraginis*.

In accordance with the present invention, the microorganisms are lactic acid bacteria belonging to the genus of *Lactobacillus*, more preferably *Lactobacillus* species as described herein. Even more preferably the *Lactobacillus* of the present invention is *Lactobacillus brevis*; another preferred *Lactobacillus* is *L. parafarraginis*. However, the *Lactobacillus* species are not limited thereto. In a particular preferred embodiment the microorganisms of the present invention are "isolated" or "purified". The term "isolated" means that the material is removed from its original environment, e.g. the natural environment if it is naturally occurring. For example, a naturally-occurring microorganism, preferably a *Lactobacillus* species, separated from some or all of the coexisting materials in the natural system, is isolated. Such a microorganism could be part of a composition, and is to be regarded as still being isolated in that the composition is not part of its natural environment.

The term "purified" does not require absolute purity; rather, it is intended as a relative definition. Individual microorganisms obtained from a library have been conventionally purified to microbiological homogeneity, i.e. they grow as single colonies when streaked out on agar plates by methods known in the art. Preferably, the agar plates that are used for this purpose are selective for *Lactobacillus* species. Such selective agar plates are known in the art.

It is especially preferred that the lactic acid bacterium is a lactic acid bacterium as filed under DSM 22721 or a fragment, a mutant and/or derivative thereof, wherein said fragment, mutant or derivative retains the capability of inhibiting the growth of a fungal organism.

In a particularly preferred embodiment of the present invention, the lactic acid bacteria of the present invention is selected from the group consisting of *Lactobacillus brevis* having DSMZ accession number DSM 22721 or a mutant or derivative thereof, wherein said mutant or derivative retains the capability to inhibit the growth of fungal organisms. The term "*Lactobacillus brevis* having DSMZ accession number" relates to cells of a microorganism belonging to the species *Lactobacillus brevis* deposited with the Deutsche Sammlung für Mikroorganismen and Zellkulturen GmbH ("DSMZ") on Jun. 26, 2009 and having the following deposit number DSM 22721. The DSMZ is located at the Mascheroder Weg 1 b, D-38124 Braunschweig, Germany. The aforementioned DSMZ deposits were made pursuant to the terms of the Budapest treaty on the international recognition of the deposit of microorganisms for purposes of patent procedure.

Fungal contamination of foods prevails as a principal problem for the food producing industry. Food preservation methods known in the state of the art such as the use of chemicals may impart undesirable properties to foods. Additionally such methods may raise concerns among consumers. Consequently, the need for alternative preservation methods has become an important issue for the food sector. Therefore the invention, especially the lactic acid bacterium as filed under DSM 22721 is of particular importance because it enables a alternative efficient method of food preservation without any side effects.

"A mutant or derivative" of the lactic acid bacteria of the present invention, preferably of the deposited *Lactobacillus brevis* has preferably the same characteristics as the respective deposited strain, i.e. it retains the capability to inhibit growth of fungal organisms, preferably with the inhibiting characteristics as described hereinabove. For example, said derivative can be genetically engineered. In the context of the present invention the term "genetically engineered" is used in its broadest sense for methods known to the person skilled in the art to modify desired nucleic acids in vitro and in vivo such that genetic modifications are affected and genes are altered by recombinant DNA technology. Accordingly, it is preferred that said methods comprise cloning, sequencing and transformation of recombinant nucleic acids. For this purpose appropriate vectors including expression vectors for *Lactobacillus* species as, for example, described in EP-B1 506 789, EP-B1 316 677, EP-B1 251 064, EP-B1-218 230, EP-B1 133 046 or WO 89/01970.

When used in the context of the present invention, the term "lactic acid bacteria of the present invention" also encompasses derivatives or mutants or analogs or fragments, such as a membrane fraction as described herein, of said microorganisms(s) which retain the above-described capability of inhibiting the growth of a fungal organism. The terms "derivative", "mutants", "analogs" and "fragments" are described elsewhere herein.

*Lactobacillus brevis* having DSMZ accession number DSM 22721 or a mutant or derivative thereof are characterized by the following specifications. The organisms show optimal growth at 30° C. to 37° C. under aerobic or anaerobic conditions. No growth can be detected above 42° C.

Aerobic fermentation of *Lactobacillus brevis* having DSMZ accession number DSM 22721 or a mutant or derivative thereof results in a higher cell density.

Cultivation of *Lactobacillus brevis* having DSMZ accession number DSM 22721 or a mutant or derivative thereof under standard conditions (e.g. MRS-Medium, 37° C., anaerobic) results in an acidification with pH 3.5-3.7.

*Lactobacillus brevis* having DSMZ accession number DSM 22721 or a mutant or derivative thereof are present as separated rods or as pairs or rarely as short chains (2-10 µm). Under standard conditions they tend to form white to cream-coloured colonies with a slightly matte appearance and a slightly structured surface.

Surprisingly the addition of the lactic acid bacteria of the invention, preferred *Lactobacillus brevis* having DSMZ accession number DSM 22721 or a mutant or derivative thereof does not change the texture or colour of the food stuff, especially yoghurt.

It is preferred that the lactic acid bacteria of the invention, preferred *Lactobacillus brevis* having DSMZ accession number DSM 22721 or a mutant or derivative thereof comprises 16S rDNA with the following sequence 1 (SEQ ID No. 1):

GCGACTTTTCGGATTATTGGGCGTAAAGCGAGCGCAGGCGGTTTTTT

AGGTCTGATGTGAAAGCCTTCGGCTTAACCGGAGAAGGGCATCGGAA

ACCGGGAGACTTGAGTGCAGAAGAGGACAGTGGAACTCCATGTGTAG

CGGTGAAATGCGTAGATATATGGAAGAACACCAGTGGCGAAGGCGGC

TGTCTGGTCTGTAACTGACGCTGAGGCTCGAAAGCATGGGTAGCGAA

CAGGATTAGATACCCTGGTAGTCCATGCCGTAAACGATGAGTGCTAA

GTGTTGGAGGGTTTCCGCCCTTCAGTGCTGCAGCTAACGCATTAAGC

ACTCCGCCTGGGGAGTACGACCGCAAGGTTGAAACTCAAAGGAATTG

ACGGGGCCCGCACAAGCGGTGGAGCATGTGGTTTAATTCGATGCTA

CGCGAAGAACCTTACCAGGTCTTGACATCTTCTGCTAACCTAAGAGA

TTAGGCGTTCCCTTCGGGGACGGAATGACAGGTGGTGCATGGTTGTC

GTCAGCTCGTGTCGTGAGATGTTGGGTTAAGTCCCGCAACGAGCGCA

ACCCTTATTGTCAGTTGCCAGCATTTAGTTGGGCACTCTGGCGAGAC

TGCCGGTGACAAACCGGAGGAAGGTGGGGATGACGTCAAATCATCAT

GCCCCTTATGACCTGGGCTACACACGTGCTACAATGGACGGTACAAC

GAGTCGCGAAACCGCGAGGTCAAGCTAATCTCTTAAAGCCGTTCTCA

GTTCGGATTGCAGGCTGCAACTCGCCTGCATGAAGTTGGAATCGCTA

GTAATCGTGGATCAGCATGCCACGGTGAATACGTTCCCGGGCCTTG

TACACACCGCCCGTCACACCATGAGAGTTTGTAACACCCAAAGCCCG

TGAGGTAACCTTCGGGAACCAGCCGTCTAAGTGGGACAGATGATTAG

GTGAAGTCGAC

Figure 2:
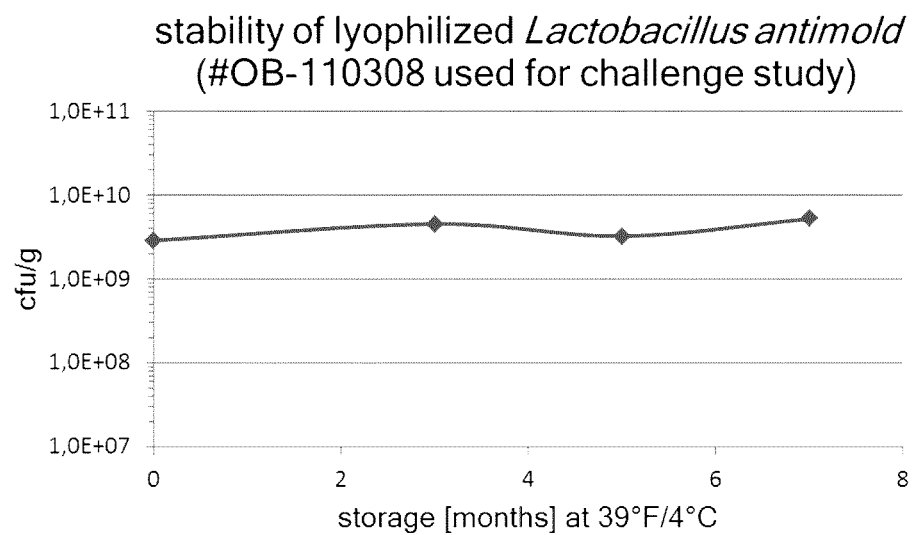
FIG. 2 shows the stability of a lyophilized lactic acid bacteria of the invention. The stability is measured via colony forming units (cfu) per g.
Figure 3:
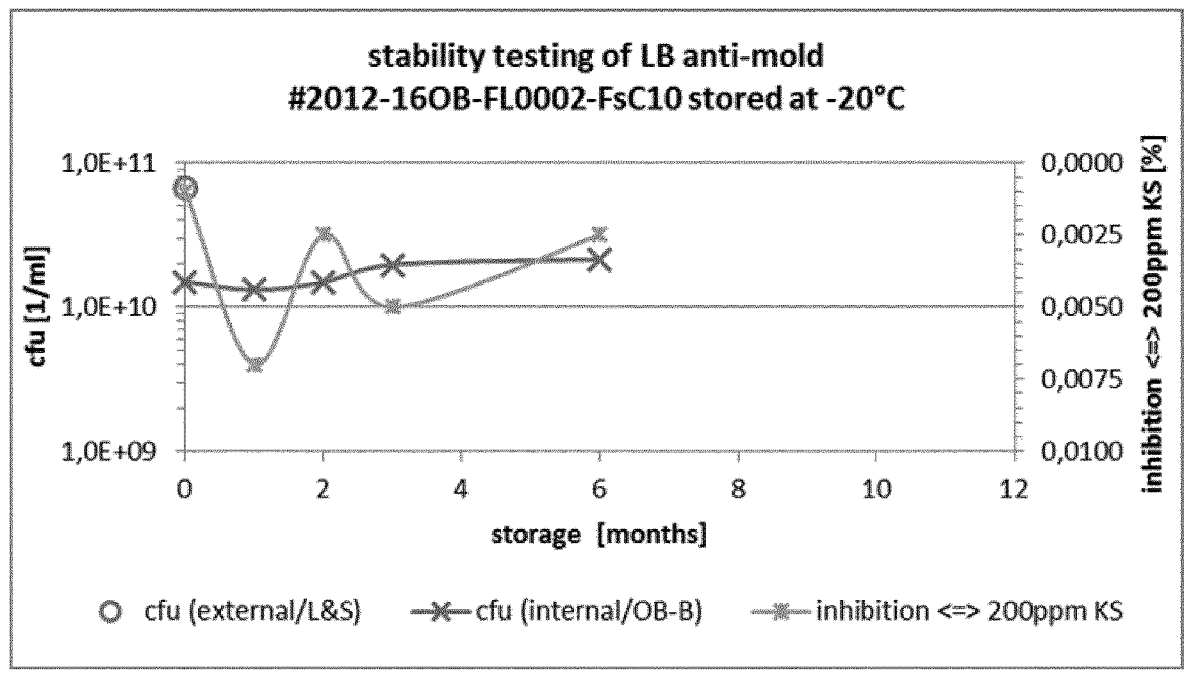
FIG. 3 shows the stability of deep frozen lactic acid bacteria of the invention after storage at negative 20° C.
Figure 4:
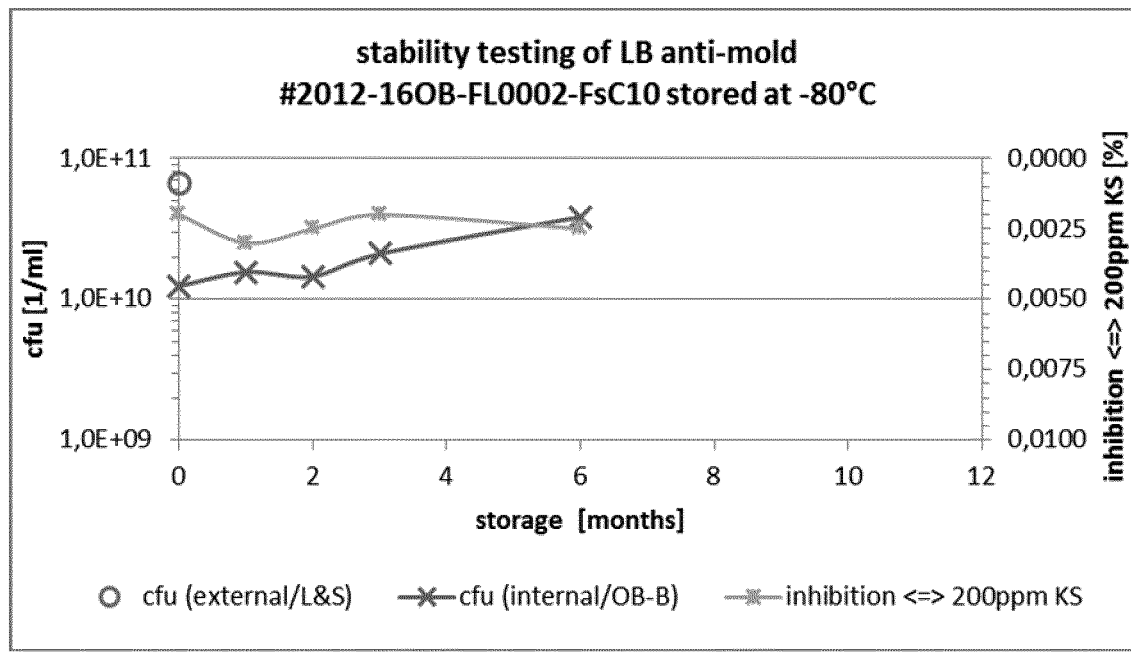
FIG. 4 shows the stability of deep frozen lactic bacteria of the invention, after storage at negative 80° C.

Another advantage of the lactic acid bacteria of the invention, preferred *Lactobacillus brevis* having DSMZ accession number DSM 22721 or a mutant or derivative thereof is that it is possible to deep freeze the strain for at least 6 months at approximatly −20° C. or approximately −80° C. The bacteria stay stable and do not lose their capability to inhibit the growth of fungal organisms. It is also possible to store the lactic acid bacteria of the invention after lyophilisation (see also FIG. 2).

One advantage is that the lactic acid bacterium of the invention, especially as filed under DSM 22721 or a fragment, a mutant and/or derivative thereof, inhibits the growth of *penicillium*, in particular *Penicillium commune* or *Penicillium roqueforti*, the genus *aspergillus* and the genus *alternaria*, in particular *Alternaria alternate*, *Penicillium expansum*, *Penicillium citrinum*, *Penicillium digitatum*, *Penicillium italicum*, *Scopulariopsis breviacaulis*, *Aspergillus flavus*, *Aspergillus parasiticus*, *Botrytis cinerea*, *rhizopus* sp., *mucor* sp., *Eurotium herbariorum*, *Geotrichum candidum*, *Cladosporium herbarum*, *Fusarium sambucinum*, *Phytophora infestans* and *Sclerotinia scerotiorum*.

In another preferred embodiment that invention related to the use said lactic acid bacteria or a fragment thereof for the production of a food composition, animal feedstuff, or a pharmaceutical or cosmetic composition, wherein the lactic acid bacteria, preferred live lactic acid bacteria, or a fragment thereof are added to the food, animal feedstuff, or a pharmaceutical or cosmetic composition.

*Lactobacillus brevis* is commonly known to use heterofermentative metabolism and therefore to be heterolactic. Heterofermentative metabolism is usually characterized by gas and acid production. Both effects are adverse for the production of food, pharmaceuticals or cosmetics. It was therefore very surprising that the lactic acid bacteria of the invention, especially *Lactobacillus brevis* having DSMZ accession number DSM 22721 or a mutant or derivative thereof show homofermentative characteristics when cultivated in cosmetic or pharmaceutical compositions or food, e.g. dairy products preferably yogurt.

The galenic preparation of a pharmaceutical composition according to the invention can be made in a way being usual in this technology. Suitable solid or liquid galenic preparation forms are for instance granulates, powders, dragees, tablets, (micro) capsules, suppositories, syrups, juices, suspensions or emulsions, for the production of which usual means are used, such as carrier substances, explosives, binding, coating, swelling, sliding or lubricating agents, tasting agents, sweeteners and solution mediators. As auxiliary substances are named here magnesium carbonate, titanium dioxide, lactose, mannite and other sugars, talcum, milk protein, gelatin, starch, cellulose and derivatives, animal and vegetable oils such as cod-liver oil, sunflower oil, peanut oil or sesame oil, polyethylene glycols and solvents, such as sterile water and mono or multi-valent alcohols, for instance glycerin. A pharmaceutical composition according to the invention can be produced by that lactic acid bacteria according to the invention are mixed in a defined dose with a pharmaceutically suitable and physiologically well tolerated carrier and possibly further suitable active, additional or auxiliary substances, and is prepared in the desired form of administration. Carriers are in particular substances, which are selected from the group comprising "maltodextrin, microcrystalline cellulose, starch, in particular corn starch, levulose, lactose, dextrose, and mixtures of such substances". The composition may contain 0.1 to 95% by weight carrier and 5 to 99.9% by weight lyophilized lactic acid bacteria, relative to the total amount of cells and carriers, or consist thereof.

*Lactobacillus brevis* having DSMZ accession number DSM 22721 or a mutant or derivative thereof are heterofermentative under standard conditions (e.g. fermentation medium or MRS medium under anaerobic conditions). This means the organisms produce gas during fermentation if they are cultivated under standard conditions.

It was therefore very surprising that *Lactobacillus brevis* having DSMZ accession number DSM 22721 or a mutant or derivative thereof present homofermentative characteristics when cultivated in dairy products, preferably yoghurt. "Standard yoghurt" was produced with standard fermentation starters at 43° C., pH 4.5-4.7 and with skim milk enriched with skimmed-milk powder. Afterwards the yoghurt is stored at 7° C. When *Lactobacillus brevis* having DSMZ accession number DSM 22721 or a mutant or derivative thereof was added to the yoghurt no gas production (gas bubbles or convex lid) can be observed. After 30 days the Off-Flavour was measured via HPLC or Head-Space-Analysis. The surprising effect of homofermentative characteristics in dairy products has the advantage that there is no change in off-flavour of the product.

Another characteristic of *Lactobacillus brevis* having DSMZ accession number DSM 22721 or a mutant or derivative thereof is that these organisms do not produce $H_2O_2$, neither under standard condition (MRS medium) nor under fermentation conditions. This was tested with $H_2O_2$-test strips.

Another advantage is that the composition of organic acids is very stable in yoghurt with added *Lactobacillus brevis* having DSMZ accession number DSM 22721 or a mutant or derivative thereof. Almost no pH-change is observed. This is especially important for the use in food stuff.

*Lactobacillus brevis* having DSMZ accession number DSM 22721 or a mutant or derivative thereof show a static growth in yogurt. "Standard yogurt" was produced with standard fermentation starters at 43° C., with skim milk enriched with skimmed-milk powder and with a final pH of 4.5-4.7. *Lactobacillus brevis* having DSMZ accession number DSM 22721 was added. The produced yoghurt was stored at 7° C. for 3 weeks. After these 3 weeks no increase of the bacteria of the invention was observed.

When using in pharmaceutical or cosmetic compositions, it is of course required that the composition does not contain any substances, in particular active substances, which substantially impair the viability of the cells and or the activity of cells, compounds, fragments or supernatants thereof employed according to the invention. The man skilled in the art of the respective substances or active substances can easily determine this by a viability test, for instance as proposed by the DSMZ, is made only in cocultivation with the respective substance or active substance in the concentration as it is in the respective composition. If this test is positive, the cells according to the invention can successfully be used. If this test is negative, the application of the respective composition is excluded, since the effect according to the invention is not achieved or to a reduced extent only. With respect to the activity, is e.g. possible to enter the pharmaceutical or cosmetic composition into an assay testing for inhibition activity, as described above, which characterizes the microorganism of the instant invention.

Cosmetic compositions are for instance shampoo, moisture cream, moisture lotion, glycolic cream, glycolic lotion, cleanser, colored makeup foundation, colored makeup powder or colored makeup concealer.

The lactic acid bacteria of the invention can be used as a direct inoculation product. Therefore the bacteria can be added to food, cosmetic or pharmaceutical compositions without any preceding processing steps. It is preferred that the bacteria of the invention are cryopreserved in their own fermentation supernatant. This facilitates the production of the products and therefore contributes to saving time and costs.

In a further preferred embodiment the invention relates to a food composition, comprising a foodstuff and said lactic acid bacteria or fragments thereof.

It is preferred that the food composition the animal feedstuff, the pharmaceutical composition or a cosmetic composition contains $10^2$ to $10^{15}$, preferably $10^6$ or $10^8$ to $10^{12}$, in particular $10^8$ to $10^{10}$ lactic acid bacteria cells or fragments thereof, absolute, or referred to 100 g of the food, animal feedstuff, or the pharmaceutical composition containing the cells. These amounts are especially beneficial because they allow a very effective inhibition of growth of fungi without any adverse effects.

It is preferred that the lactic acid bacteria are present in a concentration of 0.0001% or more. These concentrations are especially beneficial because they provide an efficient inhibition of fungal growth in food products.

It is also preferred that the food composition is a meat product or a dairy product, preferred yoghurt, milk, cheese, cream, and/or curd cheese. These products are generally prone to mould which is why the use of the lactic acid bacteria of the invention, preferably *Lactobacillus brevis* having DSMZ accession number DSM 22721 or a mutant or derivative thereof, are especially beneficial. One additional advantage is that the effect of inhibiting fungal growth is not dependent on the kind of starter culture and/or skimmed-milk powder used for the dairy, especially yogurt, production. Therefore the lactic acid bacteria of the invention can be used in various food products without losing the beneficial effect.

In another preferred embodiment the invention relates to a method for preserving foodstuff, animal feedstuff, or pharmaceutical or cosmetic composition, wherein said lactic acid bacteria are added to the foodstuff, animal feedstuff, or pharmaceutical composition.

For the preservation with lactic acid bacteria according to the invention, in principle all foods, animal feedstuff, or pharmaceutical or cosmetic compositions that may contain fungal organisms, either from production or by contamination during storage, can be used.

It is preferred that per 100 g food, animal feedstuff, or pharmaceutical or cosmetic composition, $10^2$ to $10^{15}$, preferably $10^6$ or $10^8$ to $10^{12}$, in particular $10^8$ to $10^{10}$ lactic acid bacteria cells or fragments thereof are added.

It is also preferred that the lactic acid bacteria are added in a concentration of 0.0001% to 0.01% preferably 0.001%. These concentrations are especially beneficial because they provide an efficient inhibition of fungal growth in food products. By adding lactic acid bacteria in a concentration of 0.0001% or more, preferably 0.001%, fungal growth is inhibited permanently so that the food, animal feedstuff, or pharmaceutical or cosmetic composition can be stored for a long time without losing the ability to prevent fungal growth.

It is especially preferred that 0.0001% to 0.01% preferably 0.001% pelletized, deep frozen culture of Lactobacilli of the invention are added, preferably to yogurt fermentation. The use of pelletized, deep frozen culture of Lactobacilli is advantageous for industrial production.

It is also preferred that 1 ml deep frozen culture of Lactobacilli contains $0.5 \times 10^{10}$ CFU (colony forming units).

In another preferred embodiment the invention relates to a method of identifying said lactic acid bacterium comprising h) providing a substrate,
i) providing a preparation comprising lactic acid bacteria under investigation,
j) adding the preparation comprising the lactic acid bacteria to the substrate, optionally followed by a fermentation step,
k) adding of a predetermined number of fungal spores to the product of step j), l) incubation of the test sample obtained in step l) for a predetermined duration at a predetermined temperature, m) detection, optionally followed by evaluation of fungal growth.

Another aspect of the present invention is an analog or fragment of said lactic acid bacterium which is thermally inactivated or lyophilized, wherein said analog or fragment retains the capability of inhibiting the growth of the fungal organism. The analog or fragment may in particular be present in a supernatant of a culture of the microorganisms of the invention or a fragment of such microorganism. The capability is measurable as outlined above for characterizing the microorganism of the invention.

As a further alternative for characterizing the microorganisms of the invention it is possible to employ the biocontrol assays described in the reference P. Raspor et al., Food Technol. Biotechnol. 48(3):336-343 (2010), wherein this assay is performed using microorganisms under inspection and compared to control experiments in absence of a microorganism and/or control experiments, wherein the microorganism is replaced with a conventional chemical antimould compound in defined concentration.

The growth of the fungal organism is inhibited, if with cultivation of the fungal organism without cells according to the invention, the growth of the fungal organism is increased by at least 10%, preferably by at least 50%, compared to a cocultivation of the fungal organism with the cells according to the invention under identical cultivation conditions, measured as a settlement density in a given time on a cultivation medium for the fungal organism. Additional reference is made to the specific assay described as an example only above.

Primers, enzymes, further host cells for cloning of intermediate constructs and the like can be used and are known by the skilled artisan. Preferably, genetically engineered mutants comprise cells of the microorganism of the present invention, preferably of the deposited *Lactobacillus* species harboring recombinant nucleic acids either comprised in their bacterial chromosome or one (a) plasmid(s) or comprised in their bacterial chromosome and/or (a) plasmid(s). Said recombinant nucleic acids are preferably foreign to the microorganism of the present invention. By "foreign" it is meant that the polynucleotide or nucleic acid molecule is either heterologous with respect to the host cell, this means derived from a cell or organism with a different genomic background, or is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell, in particular it is surrounded by different genes. In this case the polynucleotide may be either under the control of its own promoter or under the control of a heterologous promoter. The vector or nucleic acid molecule according to the invention which is present in the host cell may either be integrated into the genome of the host cell or it may be maintained in some form extrachromosomally. In this respect, it is also to be understood that the nucleic acid molecule of the invention can be used to restore or create a mutant gene via homologous recombination.

A mutant of the microorganism of the present invention, preferably a mutant of the deposited *Lactobacillus* strains is preferably artificially mutated. In accordance with the present invention, the term "mutated" means (a) permanent modification(s) of genetic material, i.e. nucleic acids, caused, for example, naturally or by physical means or chemical compounds/substances/agents, such as EMS or ENU. Said modifications include point mutations, like transitions or transversions, deletion/insertion/addition of one or more bases within a nucleic acid/gene/chromosome thereby modifying the nucleic acid/gene/chromosome which can cause, inter alia, aberrant gene expression/transcription/translation or inactive gene products, constitutive active/inactive gene products leading to e.g. dominant-negative effects. Preferably, a mutation leads to in increased capability of inhibiting the growth of fungal organisms. Thus, it is also preferred that the mutant cells of the deposited microorganism which harbor (a) mutation(s) in (a) desired gene(s) or in which (a) mutation(s) in (a) desired gene(s) is induced by methods known to the person skilled in the art. It is also known in the prior art that mutated or genetically engineered bacterial cells can be selected by any suitable method/phenotype. In the context of the present invention, a mutant having an increased capability of inhibiting growth of fungal organisms can be tested in accordance with the methods described in the examples herein. The term "mutant", however, also includes cells of the microorganism of the present invention, preferably cells of the deposited microorganism which harbor naturally-occurring, spontaneous mutations in their genome, i.e. bacterial chromosome. "Spontaneous mutations" are mutations that arise naturally, i.e., without direct genetic manipulation by man, or by exposure to a mutagen. Selection of spontaneous mutants can be accomplished by culturing the strain and selecting the desired variants by, for example, the variant bacterium's capability to show an improved growth. Methods for selection of spontaneous mutants are well known in the art (see, for example, Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989)). For example, such mutations may occur during cultivation, for example, during the normal cell division process coupled with DNA replication or during passaging and/or preserving the mutant of the microorganism of the present invention.

In another aspect the present invention relates to an analog or fragment of the microorganism of the present invention, which is thermally inactivated or lyophilized, wherein said analog retains the capability of inhibiting the growth of fungal organisms.

According to the present invention the term "analog of the microorganism of the present invention" includes also a dead or inactivated cell of the microorganism of the present invention, preferably of the *Lactobacillus* species disclosed herein which is no longer capable to form a single colony on a plate specific for microorganisms belonging to the genus of *Lactobacillus*. Said dead or inactivated cell may have either an intact or broken cell membrane. Methods for killing or inactivating cells of the microorganism of the present invention are known in the art. El-Nezami et al., J. Food Prot. 61 (1998), 466-468 describes a method for inactivating *Lactobacillus* species by UV-irradiation. Preferably, the cells of the microorganism of the present invention are thermally inactivated or lyophilised. Lyophilization of the cells of the present invention has the advantage that they can be easily stored and handled while retaining their capability of inhibiting the growth of fungal organisms. Moreover, lyophilised cells can be grown again when applied under conditions known in the art to appropriate liquid or solid media. Lyophilization is done by methods known in the art. Preferably, it is carried out for at least 2 hours at room temperature, i.e. any temperature between 16° C. and 25° C. Moreover, the lyophilized cells of the microorganism of the present invention are stable for at least 4 weeks at a temperature of 4° C. so as to still inhibit a fungal organism as described herein. Thermal inactivation can be achieved by incubating the cells of the microorganism of the present invention for at least 2 hours at a temperature of 170° C. Yet, thermal inactivation is preferably achieved by autoclaving said cells at a temperature of 121° C. for at least 20 minutes in the presence of saturated steam at an atmospheric pressure of 2 bar. In the alternative, thermal inactivation of the cells of the microorganism of the present invention is achieved by freezing said cells for at least 4 weeks, 3 weeks, 2 weeks, 1 week, 12 hours, 6 hours, 2 hours or 1 hour at −20° C. It is preferred that at least 70%, 75% or 80%, more preferably 85%, 90% or 95% and particularly preferred at least 97%, 98%, 99% and more particularly preferred, 99.1%, 99.2%, 99.3%, 99.4%, 99.5%, 99.6%, 99.7%, 99.8% or 99.9% and most particularly preferred 100% of the cells of the analog of the microorganism of the present invention are dead or inactivated, however, they have still the capability of inhibiting the growth of fungal organisms. Whether the analog or fragment of the microorganism of the present invention is indeed dead or inactivated can be tested by methods known in the art, for example, by a test for viability.

The term "analog of the microorganism of the present invention" encompasses lysates or fractions of the microorganism of the present invention, preferably of the *Lactobacillus* species disclosed herein. According to the present invention the term "lysate" means a solution or suspension in an aqueous medium of cells of the microorganism of the present invention that are broken. However, the term should not be construed in any limiting way. The cell lysate comprises, e.g., macromolecules, like DNA, RNA, proteins, peptides, carbohydrates, lipids and the like and/or micromolecules, like amino acids, sugars, lipid acids and the like, or fractions of it. Additionally, said lysate comprises cell debris which may be of smooth or granular structure. Methods for preparing cell lysates of microorganism are known in the art, for example, by employing French press, cells mill using glass or iron beads or enzymatic cell lysis and the like. In addition, lysing cells relates to various methods known in the art for opening/destroying cells. The method for lysing a cell is not important and any method that can achieve lysis of the cells of the microorganism of the present invention may be employed. An appropriate one can be chosen by the person skilled in the art, e.g. opening/destruction of cells can be done enzymatically, chemically or physically. Non-limiting examples for enzymes and enzyme cocktails are proteases, like proteinase K, lipases or glycosidases; non-limiting examples for chemicals are ionophores, detergents, like sodium dodecyl sulfate, acids or bases; and non-limiting examples of physical means are high pressure, like French-pressing, osmolarity, temperature, like heat or cold. Additional, a method employing an appropriate combination of an enzyme other than the proteolytic enzyme, an acid, a base and the like may also be utilized. For example, the cells of the microorganism of the present invention are lysed by freezing and thawing, more preferably freezing at temperatures below −70° C. and thawing at temperatures of more than 30° C., particularly freezing is preferred at temperatures below −75° C. and thawing is preferred at temperatures of more than 35° C. and most preferred are temperatures for freezing below −80° C. and temperatures for thawing of more than 37° C. It is also preferred that said freezing/thawing is repeated for at least 1 time, more preferably for at least 2 times, even more preferred for at least 3 times, particularly preferred for at least 4 times and most preferred for at least 5 times.

Accordingly, those skilled in the art can prepare the desired lysates by referring to the above general explanations, and appropriately modifying or altering those methods, if necessary. Preferably, the aqueous medium used for the lysates as described is water, physiological saline, or a buffer solution. An advantage of a bacterial cell lysate is that it can be easily produced and stored cost efficiently since less technical facilities are needed.

According to the invention, lysates are also preparations of fractions of molecules from the above-mentioned lysates. These fractions can be obtained by methods known to those skilled, in the art, e.g., chromatography, including, e.g., affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or other proteinchemical, molecular biological, biochemical, immunological, chemical or physical methods to separate above components of the lysates.

"A fragment of the microorganism of the present invention" encompasses any part of the cells of the microorganism of the present invention. Preferably, said fragment is a membrane fraction obtained by a membrane-preparation. Membrane preparations of microorganisms belonging to the genus of *Lactobacillus* can be obtained by methods known in the art, for example, by employing the method described in Rollan et al., Int. J. Food Microbiol. 70 (2001), 303-301, Matsuguchi et al., Clin. Diagn. Lab. Immunol. 10 (2003), 259-266 or Stentz et al., Appl. Environ. Microbiol. 66 (2000), 4272-4278 or Varmanen et al., J. Bacteriology 182 (2000), 146-154. Alternatively, a whole cell preparation is also envisaged. Preferably, the herein described derivative or fragment of the microorganism of the present invention retains the capability of inhibiting the growth of fungal organisms which is described in detail herein.

The invention is based first of all on the finding of *Lactobacillus* strains, which are capable of extending the shelf life of the yogurt by the inhibition of fungal growth. By using such a *Lactobacillus* strain, the preservation agent potassium sorbate, employed up to now, can be replaced. In experiments, the inhibition activity of *Lactobacillus* cells with respect to fungi of the species *penicillium, aspergillus* and *alternaria* was tested. First, living *Lactobacillus* cells with respect to an antifungal activity were used. A *Lactobacillus* strain (*Lactobacillus brevis*) was identified, which is capable to inhibit the growth of the tested fungal strains. The bacterium was designated "*Lactobacillus* antimold" and submitted to the DSMZ (Deutsche Sammlung von Mikroorganismen and Zellkulturen GmbH) under the designation DSM 22721 on Jun. 26, 2009.

In another experiment, the *Lactobacillus* strain was tested in a food. For this purpose, the *Lactobacillus* strain was added together with a yogurt starter culture to a starting medium for the yogurt production. After fermentation of the yogurt, fungal spores were added, and the yogurt was stored at 7° C. Compared to control batches with and without addition of potassium sorbate as a preservation agent, it was found that in the batch with *Lactobacillus* of the invention a significant extension of the durability has been achieved, i.e. the growth of the fungus could be inhibited over a clearly longer period of time than with potassium sorbate.

Using such a *Lactobacillus* strain for the preservation of foods, animal feedstuff or pharmaceutical or cosmetic compositions has a decisive advantage over the common preservation methods. It is a biological preservation agent which does not alter the flavour or texture of the food.

The invention further relates to the use of microorganism cells according to the invention for producing a preserved food, an animal feedstuff, or a pharmaceutical or cosmetic composition, wherein to the food, animal feedstuff, or pharmaceutical or cosmetic composition the microorganism cells are added, and to a method for preserving a food, an animal feedstuff, or a pharmaceutical or cosmetic composition, wherein to the food, animal feedstuff, or pharmaceutical or cosmetic composition the microorganism cells according to the invention are added.

The application of microorganism cells according to the invention is simple, in the case of foods the (living) cells, or the fragments or analogs of the bacteria of the invention are added in the specified amount to the food. Analogous considerations apply to animal feedstuff or pharmaceutical compositions.

EXAMPLES

In the following, the invention is described in more detail with reference to examples without being limited to these examples.

Example 1

Inhibition of Fungi in Foods

Used materials:

The used cultures were: yogurt starter culture Yo-Mix 401 (Danisco, Denmark), *Lactobacillus* DSM 22721, *Penicillium commune*, *Penicillium roqueforti*, *Anternaria alternata* and other own isolates such as *aspergillus*.

The used chemicals or media were:

Ultra-high temperature treated homogenized milk, 1.5% fat, e.g. from Campina Mark Brandenburg, Instant skimmed-milk powder "frema Reform" from Granovita GmbH, D-87751 Heimertingen (obtainable from Reformhaus Demski), Potassium sorbate solution 20 mg/ml (VWR International GmbH, Darmstadt), sterile-filtrated, YDA bouillon (yeast extract PTU (Ohly GmbH) 25.0 g/l, D(+) glucose monohydrate (Merck, Darmstadt) 20.0 g/l, Tween 80 (Merck, Darmstadt) 1.0 g/l, di-ammonium hydrogen citrate (Merck, Darmstadt) 2.0 g/l, sodium acetate (Merck, Darmstadt) 5.0 g/l, magnesium sulfate heptahydrate (Merck, Darmstadt) 0.1 g/l, manganese (II) sulfate monohydrate (Sigma-Aldrich, Seelze) 0.05 g/l, di-potassium hydrogen phosphate (Merck, Darmstadt) 2.0 g/l, autoclaving at 121° C. for 20 min, pH 5.7 after autoclaving, Artificial yogurt medium (aYH medium), D(+) glucose monohydrate (Merck, Darmstadt) 22 g/l, Biospringer 0207/0-MG-L yeast extract (Biospringer, Maisons-Afort Cedex, France) 15 g/l, skimmed-milk powder (Granovita GmbH, Heimertingen) 20 g/l, Tween 80 (Merck, Darmstadt) 1.0 g/l, di-ammonium hydrogen citrate (Merck, Darmstadt) 2.0 g/l, sodium acetate (Merck, Darmstadt) 5.0 g/l, magnesium sulfate heptahydrate (Merck, Darmstadt) 0.1 g/l, manganese (II) sulfate monohydrate (Sigma-Aldrich, Seelze) 0.05 g/l, di-potassium hydrogen phosphate (Merck, Darmstadt) 2.0 g/l, Yogurt medium (ultra-high temperature treated milk (1.5% fat)+2.0% w/w Bio skimmed milk), MRS bouillon (MRS Lactobacilli broth (BD Difco, Augsburg) 55 g/l, pH 6.5), Potato dextrose agar (potato dextrose broth (BD Difco, Augsburg) 24 g/l, agar, granulated (BD Difco, Augsburg) 1.5 g/l, pH 5.1), and Cryoprotection solution (Glucose monohydrate (Merck, Darmstadt) 80 g/l, peptone trypticase (BD Difco, Augsburg) 2 g/l, magnesium heptahydrate (Merck, Darmstadt) 10 g/l, potassium di-hydrogen phosphate (Merck, Darmstadt) 4 g/l, sodium nitrate (Merck, Darmstadt) 6 g/l, potassium chloride (Merck, Darmstadt) 1 g/l, iron (II) sulfate heptahydrate (Merck, Darmstadt) 0.02 g/l, glycerin (85%) (Merck, Darmstadt) 200 g/l, pH 5.6).

Used methods:

The starter cultures were prepared by dissolving 1 g lyophilized yogurt starter (Yo-Mix 401, Danisco, Denmark) in 500 ml ultra-high temperature treated low-fat milk and letting it swell for 20 min at ambient temperature.

The pre-cultivation of *Lactobacillus* according to the invention was performed by inoculating 9 ml YDA bouillon with 1.5 ml deep-freeze culture, followed by anaerobic incubation at 37° C. for 48 h.

The main cultivation of *Lactobacillus* according to the invention was performed by inoculating 30 ml YDA bouillon with the pellet from 8 ml of the pre-cultivation, followed by anaerobic incubation at 37° C. for 24 h.

The fermentation of *Lactobacillus* according to the invention was performed by centrifuging 28 ml of the main culture for 5 min at 4,500 rpm, and the supernatant was discarded. The obtained pellet was re-suspended in 5 ml sterile 0.9% NaCl solution and completely transferred into a 1 l Erlenmeyer flask with 0.5 l aYH medium. Subsequently an anaerobic incubation was performed at 37° C. for 24 h on an agitator at 150 rpm. After fermentation, the pH value was adjusted to a value of 5.5±0.1 with 2 M KOH.

For producing the yogurt, 100 ml ultra-high temperature treated milk (1.5% fat)+2.0 g skimmed-milk powder (2% w/w) were filled into a Schott flask. Then the mixture was heated to 110° C. for 15 min in an autoclave. After cooling-down to 42° C., 0.5 ml freshly produced yogurt starter culture was added. Thereafter, an anaerobic incubation was performed at 42° C. to obtain a pH value of 4.6±0.1. Storage until further use was made at 7° C.

For producing a cryogenic fungal spore suspension, a fungus sample was plated-out on potato dextrose agar, followed by cultivation for 1-4 weeks at 25-30° C. under aerobic conditions until sporulation. Then the culture was submerged in 10 ml cryoprotection culture, the liquid supernatant was removed and transferred into cryotubes. Storage of the cryocultures was made at −80° C.

For preparing the fungus for the bioassay, 0.1 ml of the cryogenic fungal spore suspension was plated-out on potato dextrose agar, followed by cultivation for 1-4 weeks at 25-30° C. under aerobic conditions until sporulation. Then the culture was submerged in 10 ml of a 0.1% Tween 80 solution. The liquid supernatant was transferred into Falcon tubes and stored at 4-6° C. A dilution of the suspension was performed with H2Odist to 250 spores/ml.

The bioassay for the inhibition of fungi by the *Lactobacillus* on potato dextrose agar was made by plating-out 200 µl of a spore suspension with 250 spores/ml onto a potato dextrose agar plate. After drying, 5 holes were drilled in the agar plate by means of a cork drill. 40 µl each of the following mixtures were pipetted:

1) 24 h *Lactobacillus* culture in MRS medium,
2) supernatant from 24 h *Lactobacillus* culture in MRS medium,
3) *Lactobacillus* from 24 h culture in MRS, granulated and re-suspended in PBS buffer (→cells in PBS),
4) MRS medium,
5) PBS.

Subsequently an anaerobic cultivation of the plate was performed at ambient temperature for up to 14 days.

The bioassay for proving the inhibition of fungi by *Lactobacillus* in yogurt was made by putting 40 ml yogurt medium in a falcon tube. Then 0.2 ml starter culture was added. As samples were provided:
1) addition of 1×108 *Lactobacillus* cells,
2) control A without *Lactobacillus*, and
3) control B without *Lactobacillus*, with post-fermentative addition of 0.4 ml potassium sorbate solution.

Then followed one fermentation each at 42° C. up to pH=4.6±0.1 with subsequent cooling-off to 7° C., filling of 6-well plates with 8 ml each of the samples, addition of 50 spores per sample (controls without spores), incubation at 7° C. and daily visual inspection for fungus growth. As an alternative for the visual inspection an automated evaluation may be performed using a digital camera, wherein a preset contrast setting is used, which distinguishes the fungi from the underlying substrate. This allows carrying out a pixel count of such pixels, which are below or above a predetermined brightness threshold and, thus, are related with fungal growth. The number of pixels can then be set into a ratio to the total number of pixels related with a sample, providing a quantitative measure of the amount of fungi present in the tested sample. As a camera the FluorChem® FC2 Imaging System (Alpha Innotech/Cell Biosciences), Santa Clara, USA) system is suitable with the following settings: Exposure time: 100-150 ms, aperture: 8, contrast settings: black level: 55000, white level: 60000, gamma: 3.0, light settings: trans-light "on", reflected-light "on", chemi display "on", speed/resolution: normal/ultra. Images were analyzed with the AlphaEaseFC software.

Inhibition of fungal growth by *Lactobacillus* cells according to the invention.

The bioassay for verifying the inhibition of fungal growth by *Lactobacillus* according to the invention in yogurt was carried out with the following results. After 7 days, fungal growth was detected by visual inspection in samples without *Lactobacillus* or potassium sorbate (control A). After 9 days, fungal growth was also detected by visual inspection in samples with potassium sorbate (control B). Only after 28 days however, fungal growth was also detected in samples with the *Lactobacillus* cells according to the invention. The result is that a distinct reduction of fungal growth by *Lactobacillus* cells according to the invention is achieved, and thus a substantial extension of the durability of the yogurt.

Example 2

Fungal spores were collected form inoculated yogurt surfaces and cultivated on an fungal optimized medium (Potato Dextrose Agar) under optimized conditions (25° C., aerobic, 5 days). The use of 0.1% *Lactobacillus brevis* DSM 22721 resulted in no fungal growth at all (compare FIG. 1; (13). The effect of *Lactobacillus brevis* DSM 22721 is fungicide and not fungistatic. This experiment also showed that the effect of *Lactobacillus brevis* DSM 22721 is superior to potassium sorbate (compare FIG. 1: potassium sorbate 11, without potassium sorbate 10).

Example 3

Preparation of Spore Suspension

For producing a cryogenic fungal spore suspension, a fungus sample was plated-out on potato dextrose agar, followed by cultivation for 1-4 weeks at 25-30° C. under aerobic conditions until sporulation. Then the culture was submerged in 10 ml cryoprotection culture, the liquid supernatant was removed and transferred into cryotubes. Storage of the cryocultures was made at −80° C.

For the preparation of spores for the bioassay, the spore suspension was prepared at $5*10^6$/mL in potato dextrose broth.

Preparation of *Lactobacillus* Cells:

The *Lactobacillus* culture was cultivated in YDA medium for 24 h at 37° C. Subsequently the cells were harvested by centrifugation at 4000×g, before the cells were washed with $dH_2O$. Afterwards the cells were 10-fold concentrated in $dH_2O$.

Preparation of Co-Incubation Assay:

For the co-Incubation assay, 980 µl of a *P. commune* spore suspension containing $5*10^6$/mL of spores and 20 µl of a 10-fold *Lactobacillus* concentrate were co-incubated at 25° C. for 24 h in a 24-well plate. The germination rate of spores was determined at different time points by microscopic evaluation of samples in a thoma chamber. Therefore at least 100 spores were evaluated and the percentage of germinated spores was calculated. A spore was determined as germinated in case the length of the outgrowth exceeded the diameter of the spore.

Results are shown in FIG. 5: Germination rate in [%] of *P. commune* spores after co-incubation with and without *Lactobacillus* cells. An inhibition of germination was regarded as significant if the germination of at least 10% of spores was inhibited.

The invention claimed is:

1. A method for inhibiting growth of at least one fungal organism in a food composition, animal feedstuff, a pharmaceutical composition or a cosmetic composition, the method comprising:
providing lactic acid bacteria deposited at DSMZ (Deutsche Sammlunq fuer Mikroomanismen and Zellkulturen GmbH) on Jun. 26, 2009 under accession no. DSM 22721 or a lysate thereof, wherein said lactic acid bacteria is capable of anaerobic growth at 37° C., and adding said lactic acid bacteria or said lysate thereof to the food composition, animal feedstuff, pharmaceutical composition or cosmetic composition, wherein the lactic acid bacteria or lysate thereof, inhibits the growth of at least one fungal organism in said food composition, animal feedstuff, pharmaceutical composition or cosmetic composition.

2. The method of claim 1, wherein the food composition is a meat product or a dairy product.

3. A method for preserving foodstuff, animal feedstuff, a pharmaceutical composition or a cosmetic composition, the method comprising adding the lactic acid bacteria deposited at DSMZ (Deutsche Sammlunq fuer Mikroomanismen and Zellkulturen GmbH) on Jun. 26, 2009 under accession no. DSM 22721 or a lysate thereof to the foodstuff, animal feedstuff, pharmaceutical composition or cosmetic composition, wherein the lactic acid bacteria or lysate thereof preserves the foodstuff, animal feedstuff, pharmaceutical or cosmetic composition, and wherein said lactic acid bacteria is capable of anaerobic growth at 37° C.

4. The method according to claim 3, wherein the lactic acid bacteria are live lactic acid bacteria.

5. The method according to claim 3, wherein the lactic acid bacteria or lysate thereof comprises $10^2$ to $10^{15}$ lactic acid bacteria cells per 100 g food composition, animal feedstuff, pharmaceutical composition or cosmetic composition.

6. The method of claim 5, wherein the lactic acid bacteria or lysate thereof comprises $10^8$ to $10^{12}$ lactic acid bacteria cells per 100 g food, animal feedstuff, pharmaceutical composition or cosmetic composition.

7. The method according to claim 5, wherein the lactic acid bacteria or lysate thereof is added to a concentration of 0.0001 wt % to 0.01 wt %.

8. The method according to claim 7, wherein the lactic acid bacteria or lysate thereof is added to a concentration of 0.0001 wt % to 0.001 wt %.

* * * * *